(12) United States Patent
Dinsmore

(10) Patent No.: US 6,721,392 B1
(45) Date of Patent: Apr. 13, 2004

(54) OPTICALLY DRIVEN THERAPEUTIC RADIATION SOURCE INCLUDING A NON-PLANAR TARGET CONFIGURATION

(75) Inventor: Mark Dinsmore, Sudbury, MA (US)

(73) Assignee: Carl-Zeiss-Stiftung, Okerkochen (DE)

( * ) Notice: Subject to any disclaimer, the term of this patent is extended or adjusted under 35 U.S.C. 154(b) by 11 days.

(21) Appl. No.: 10/005,289

(22) Filed: Dec. 4, 2001

(51) Int. Cl.$^7$ .................................................. A61N 5/10
(52) U.S. Cl. .......................................... 378/65; 378/119
(58) Field of Search .......................... 378/65, 119, 136, 378/143, 138

(56) References Cited

U.S. PATENT DOCUMENTS

| | | |
|---|---|---|
| 5,090,043 A | 2/1992 | Parker et al. |
| 5,153,900 A | 10/1992 | Nomikos et al. |
| RE34,421 E | 10/1993 | Parker et al. |
| 5,369,679 A | 11/1994 | Sliski et al. |
| 5,422,926 A | 6/1995 | Smith et al. |
| 5,428,658 A | 6/1995 | Oettinger et al. ........... 378/119 |
| 5,621,780 A | 4/1997 | Smith et al. |
| 6,319,188 B1 | 11/2001 | Lovoi |
| 6,320,935 B1 | 11/2001 | Shinar et al. |
| 6,324,257 B1 | 11/2001 | Halavee |
| 6,480,573 B1 * | 11/2002 | Dinsmore ................... 378/136 |
| 6,493,419 B1 * | 12/2002 | Dinsmore ................... 378/65 |

FOREIGN PATENT DOCUMENTS

| | | |
|---|---|---|
| WO | WO 93/04735 | 3/1993 |
| WO | WO 01/47596 | 7/2001 |

\* cited by examiner

Primary Examiner—Louis M. Arana
(74) Attorney, Agent, or Firm—McDermott, Will & Emery

(57) ABSTRACT

A minaturized tharapeutic radiation source includes a optically driven thermionic cathode having an electron-emissive surface, and a non-planar, x-ray emissive target. A fiber optic cable directs a beam of optical radiation, having a power level sufficient to heat at least a portion of the electron-emissive surface to an electron emitting temperature, from a laser source onto the cathode. An electron beam emitted from said cathode strikes the target, positioned in the electron beam path. The target includes a thin film of x-ray emissive material, adapted to emit therapeutic radiation in response to incident accelerated electrons from the electron beam, and a support structure made of x-ray transmissive material. The target has a non-planar configuration, such as a conical shape or a hemispherical shape, designed to produce a more uniform and intense radiation pattern around the target.

22 Claims, 4 Drawing Sheets

OPTICALLY DRIVEN THERAPEUTIC RADIATION SOURCE INCLUDING A NON-PLANAR TARGET CONFIGURATION

CROSS-REFERENCE TO RELATED APPLICATIONS

Not Applicable

STATEMENT REGARDING FEDERALLY SPONSORED RESEARCH

Not Applicable

REFERENCE TO MICROFICHE APPENDIX

Not Applicable

FIELD OF THE INVENTION

The present invention relates to therapeutic radiation sources, and more particularly to miniaturized, optically driven therapeutic radiation sources.

BACKGROUND OF THE INVENTION

In the field of medicine, therapeutic radiation such as x-ray radiation and γ-ray radiation is used for diagnostic, therapeutic and palliative treatment of patients. The conventional medical radiation sources used for these treatments include large, fixed position machines as well as small, transportable radiation generating probes. The current state-of-the-art treatment systems utilize computers to generate complex treatment plans.

Conventional radiation systems used for medical treatment utilize a high power remote radiation source, and direct a beam of radiation at a target area, such as a tumor inside the body of a patient. This type of treatment is referred to as teletherapy because the radiation source is located a pre-defined distance from the target. This treatment suffers from the disadvantage that tissue disposed between the radiation source and the target is exposed to radiation. Teletherapy radiation sources, which apply radiation to target regions internal to a patient from a source external to the target regions, often cause significant damage not only to the target region or tissue, but also to all surrounding tissue between the entry site, the target region, and the exit site.

Brachytherapy, on the other hand, is a form of treatment in which the source of radiation is located close to or in some cases within the area receiving treatment. Brachytherapy, a word derived from the ancient Greek word for close ("brachy"), offers a significant advantage over teletherapy, because the radiation is applied primarily to treat only a predefined tissue volume, without significantly affecting the tissue adjacent to the treated volume. The term brachytherapy is commonly used to describe the use of radioactive "seeds," i.e. encapsulated radioactive isotopes, which can be placed directly within or adjacent the target tissue to be treated. Handling and disposal of such radioisotopes, however, may impose considerable hazards to both the handling personnel and the environment.

The term "x-ray brachytherapy" is defined for purposes of this application as x-ray radiation treatment in which the x-ray source is located close to or within the area receiving treatment. An x-ray brachytherapy system, which utilizes a miniaturized low power radiation source that can be inserted into, and activated from within, a patient's body, is disclosed in U.S. Pat. No. 5,153,900 issued to Nomikos et al., U.S. Pat. No. 5,369,679 to Sliski et al., and U.S. Pat. No. 5,422,926 to Smith et al., all owned by the assignee of the present application, all of which are hereby incorporated by reference.

The x-ray brachytherapy system disclosed in the above-referenced patents includes a miniaturized, insertable probe which is capable of generating x-ray radiation local to the target tissue, so that radiation need not pass through the patient's skin, bone, or other tissue prior to reaching the target tissue. The insertable probe emits low power x-rays from a nominal "point" source located within or adjacent to the desired region to be affected. In x-ray brachytherapy, therefore, x-rays can be applied to treat a predefined tissue volume without significantly affecting the tissue adjacent to the treated volume. Also, x-rays may be produced in pre-defined dose geometries disposed about a predetermined location. X-ray brachytherapy offers the advantages of brachytherapy, while avoiding the use and handling of radioisotopes. Also, x-ray brachytherapy allows the operator to control over time the dosage of the delivered x-ray radiation.

X-ray brachytherapy typically involves positioning the insertable probe into or adjacent to the tumor, or into the site where the tumor or a portion of the tumor was removed, to treat the tissue adjacent the site with a local boost of radiation. X-ray probes of the type generally disclosed in U.S. Pat. No. 5,153,900 include a housing, and a hollow, tubular probe or catheter extending from the housing along an axis and having an x-ray emitting target at its distal end. The probe may enclose an electron source, such as a thermionic cathode. In another form of an x-ray brachytherapy device, as disclosed in U.S. Pat. No. 5,428,658, an x-ray probe may include a flexible probe, such as a flexible fiber optic cable enclosed within a metallic sheath. In such a flexible probe, the electron source may be a photocathode. In a photocathode configuration, a photoemissive substance is irradiated by a LED or a laser source, causing the generation of free electrons. Typically, the flexible fiber optic cable couples light from a laser source or a LED to the photocathode.

The power requirements for the miniaturized x-ray brachytherapy systems can be reduced by optically driving the thermionic cathodes in the electron sources, instead of ohmically heating the thermionic cathodes. U.S. patent application Ser. No. 09/884,561 (identified by Attorney Docket Nos. PHLL-155 and hereby incorporated by reference)(hereinafter the "PHLL-155" application) discloses a miniaturized therapeutic radiation source that includes a reduced-power, increased efficiency electron source that is optically driven. The PHLL-155 application discloses an electron source that includes a thermionic cathode having an electron emissive surface. The PHLL-155 application discloses using laser energy to heat the electron emissive surface of the thermionic cathode, instead of heating the electron emissive surface of the thermionic emitter using conventional ohmic heating. In this way, electrons can be produced in a quantity sufficient to produce the electron current necessary for generating therapeutic radiation at the target, while significantly reducing the power requirements for the therapeutic devices. Electrons can be generated with minimal heat loss, without requiring a vacuum-fabricated photocathode.

Generally, when treating a targeted treatment region, such as a tumor or the body cavity or a tumor, it is desirable to uniformly radiate the entire surface of the tumor or the tissue lining the cavity, in such a way that an isodose contour is coincident with the surface of the body cavity. An isodose contour is a surface in which the absorbed radiation energy is equal at every point on the surface.

Even though the x-ray brachytherapy systems described above can generate x-rays local to the target tissue, it is difficult to provide a uniform, or other desired, dose of radiation to an irregularly shaped target tissue, using these systems. These x-ray sources generally act as point sources of therapeutic radiation. The intensity of the radiation from a point source decreases uniformly with approximately the square of the distance (R) from the source (i.e., $1/R^2$). Since body cavities, or the beds of resected tumors, are not generally spherically symmetrical, a point source within a body cavity or central to the resected tumor bed will not deliver a uniform dose of radiation to the tissue lining of the cavity or the bed. Similarly, for a non-spherical tumor, a point source at the tumor center will not deliver radiation with an isodose contour matching the peripheral surface of the tumor.

It is desirable to provide a uniform dose of radiation to the isodose contours that match the peripheral surface of a desired treatment region, using an optically driven, high efficiency x-ray brachytherapy system. It is also desirable to increase the efficiency of the miniaturized, optically driven radiation sources, described above.

It is an object of this invention to increase the uniformity and intensity of the x-ray radiation delivered by an optically driven x-ray brachytherapy system. In particular, it is an object of this invention to increase the uniformity and intensity of the x-ray radiation from an optically driven x-ray brachytherapy system, by altering the geometry and configuration of the x-ray target.

SUMMARY OF THE INVENTION

The present invention is directed to an optically driven x-ray source having a laser-heated thermionic cathode. In the present invention, the geometry and configuration of the x-ray target are designed to substantially increase the uniformity of the x-ray radiation delivered by the x-ray source onto a treatment region. In particular, an x-ray emissive target having a non-planar target geometry is utilized, in order to deliver a more uniform and more intense flux of x-ray radiation to a treatment region.

The present invention features a therapeutic radiation source that includes a radiation generator assembly, a source of optical radiation, and an optical delivery structure such as a fiber optic cable. The radiation generator assembly includes an electron source for emitting electrons to generate an electron beam along a beam path, and a target positioned in the beam path and adapted to emit therapeutic radiation in response to incident accelerated electrons from the electron beam. The electron source includes a thermionic cathode having an electron emissive surface. The fiber optic cable is adapted to transmit optical radiation, incident on an proximal end of the cable, to a distal end of the cable. The fiber optic cable directs a beam of the transmitted optical radiation upon the electron emissive surface of the cathode. The beam has a power level sufficient to heat at least a portion of the surface to an electron emitting temperature, so as to cause thermionic emission of the electrons from the surface.

The present invention features a non-planar configuration for the x-ray emitting target, in contrast to a planar, disk-shaped target. For example, the target may have a substantially conical shape, a substantially hemispherical shape, a substantially spherical shape, or a substantially convex shape. The target includes a thin film made of an x-ray emissive material, and an x-ray transmissive support structure. By fabricating the target in a non-flat configuration that includes an x-ray emissive film supported on an x-ray transmissive structure, the radiation pattern around the target can be rendered more uniform and more intense, as compared to x-ray targets in the prior art.

DETAILED DESCRIPTION

The present invention is directed to a miniaturized, low power therapeutic radiation source, which includes an electron-beam activated therapeutic radiation source, and which uses a laser-heated thermionic cathode to significantly reduce the power requirements. The present invention seeks to increase the uniformity and intensity of the x-ray radiation pattern generated by the target, by modifying the geometrical configuration of the target.

Figure 1:
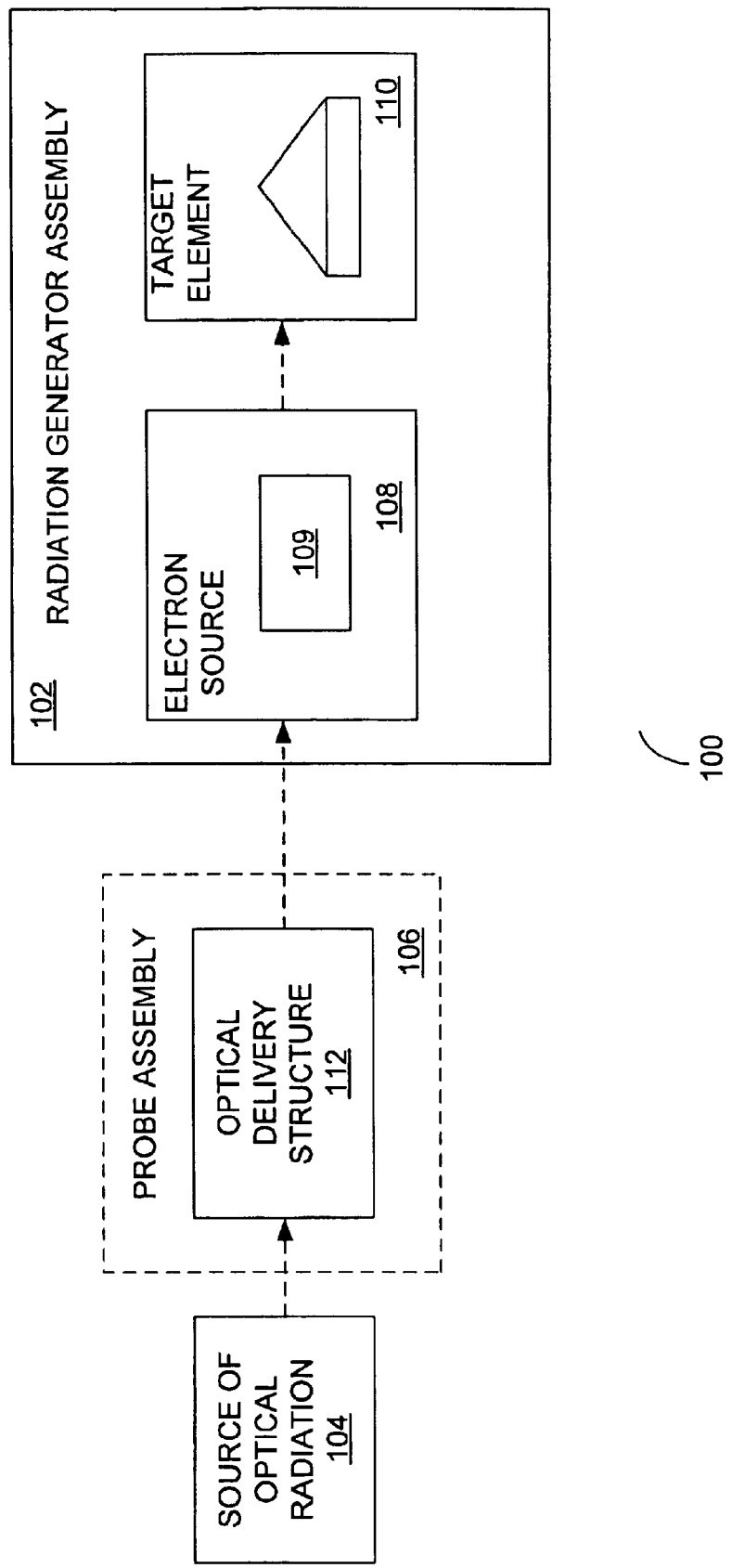
FIG. 1 is a schematic diagram of an overview of one embodiment of a therapeutic radiation source, constructed in accordance with the present invention.

FIG. 1 is a schematic block diagram of an overview of one embodiment of a therapeutic radiation source 100, constructed according to the present invention, and including an x-ray emissive target that is shaped to maximize the uniformity and intensity of the generated x-rays. In overview, the system of the present invention includes a radiation generator assembly 102, a source of optical radiation 104, and a probe assembly 106. In a preferred embodiment, the source of optical radiation 104 is a laser, so that the optical radiation generated by the source is substantially monochromatic, and coherent. The laser may be a diode laser, by way of example; however other lasers known in the art may be used, such as a Nd:YAG laser and a molecular laser.

The radiation generator assembly 102 includes an electron source 108, and a target element 110 that includes at least one radiation emissive material adapted to emit x-rays, in response to incident accelerated electrons from the electron beam. In the present invention, the target element 110 has a non-planar configuration, which renders the radiation pattern of the emitted x-rays more intense and more uniform, as compared to planar target elements. The electron source 108 includes a thermionic cathode 109. The probe assembly 106 includes an optical delivery structure 112, such as a fiber optical cable assembly. The optical delivery structure 112 directs a beam of laser radiation generated by the laser 104 onto the electron source 108. The laser beam heats the thermionic cathode 109 in the electron source 108, so as to cause thermionic emission of electrons.

Generally, the apparatus of the present invention operates at voltages in the range of approximately 10 keV to 90 keV, and electron beam currents in the range of approximately 1 nA to 100 µA. At those operating voltages and currents, radiation output is relatively low, and the apparatus may be made small enough to be adapted for implantation in medical therapeutic applications. In view of the low-level radiation output, adequate tissue penetration and cumulative dosage may be attained by positioning the radiation source adjacent to or within the region to be irradiated. Thus, therapeutic radiation is emitted from a well-defined, small source located within or adjacent to the region to be irradiated.

Figure 2A:
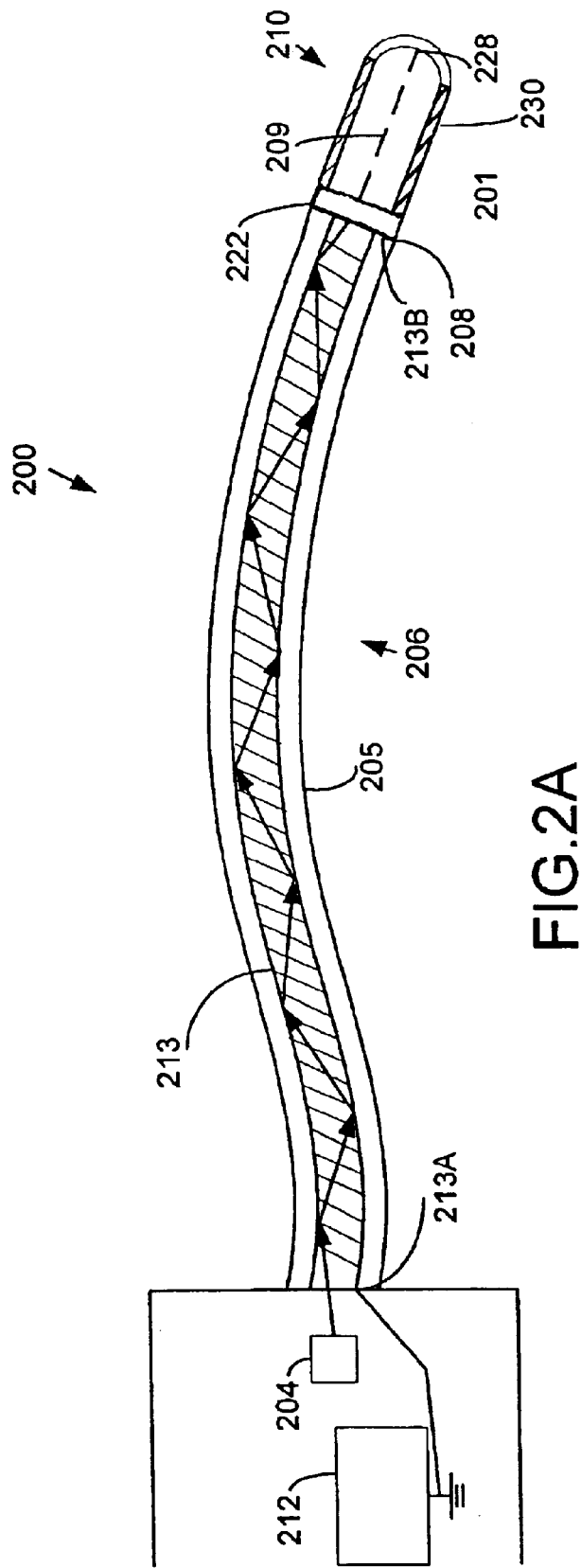
FIG. 2A is an overall diagrammatic view of one embodiment of a therapeutic radiation source constructed according to the present invention.
Figure 2B:
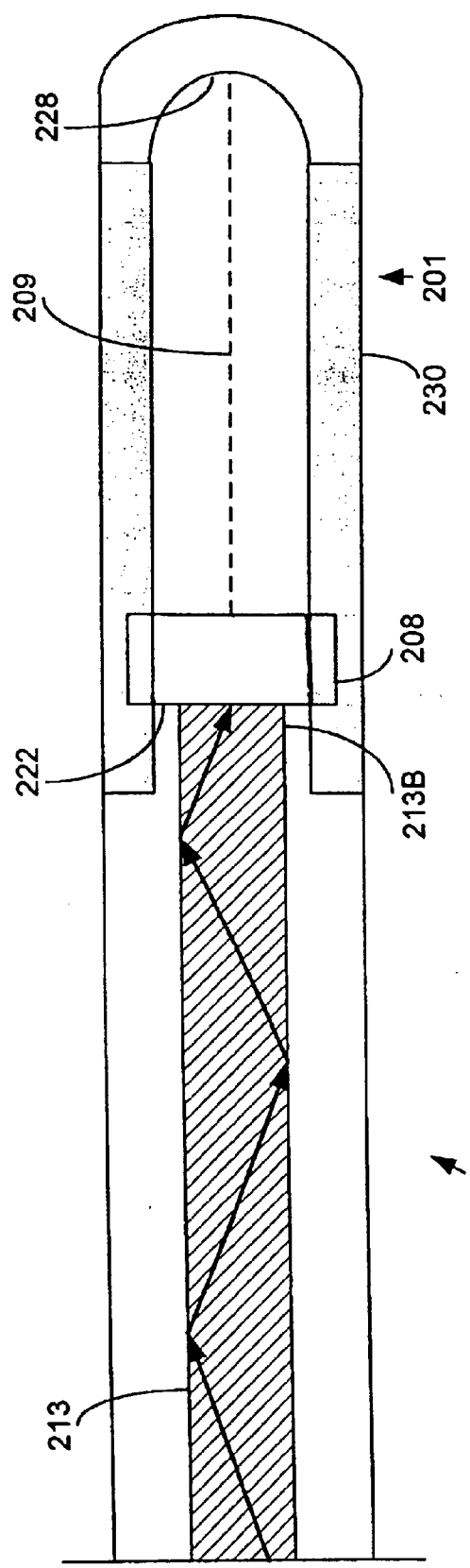
FIG. 2B provides an enlarged view of the radiation generator assembly, and the distal end of the probe assembly, constructed in accordance with the present invention.

FIGS. 2A and 2B show a diagrammatic view of one embodiment of the therapeutic radiation source apparatus 200 constructed according to the present invention. In the embodiment illustrated in FIG. 2A, the apparatus 200 includes a laser source 204, a probe assembly 206, and a radiation generator assembly 201. FIG. 2A provides an overall view of the therapeutic radiation source 200, whereas FIG. 2B provides an enlarged view of 1) the radiation generator assembly 201, and 2) the distal end of the probe assembly 206. As seen from FIG. 2A, the probe assembly 206 couples both the laser source 204 and the high voltage power supply 212 to the target assembly 210.

The radiation generator assembly 201 includes an electron source 208 that generates an electron beam along a beam path 209, and a target assembly 210 positioned in the beam path. In the illustrated embodiment, a high voltage power supply 212 is also provided. Referring to both FIGS. 2A and 2B, the electron source 208 includes a thermionic cathode 222 having an electron emissive surface.

The high voltage power supply 212 may establish an acceleration potential difference between the thermionic cathode 222 and the grounded target element 228, so that electrons emitted from the thermionic cathode 222 are accelerated toward the target element 228, and an electron beam is generated. The electron beam is preferably thin (e.g. 1 mm or less in diameter), and is established along a beam path 209 along a nominally straight reference axis that extends to the target assembly 210. The target assembly 210 is positioned in the beam path 209. The distance from the electron source 208 to the target assembly 210 is preferably less than 2–5 mm.

The high voltage power supply 212 preferably satisfies three criteria: 1) small in size; 2) high efficiency, so as to enable the use of battery power; and 3) independently variable x-ray tube voltage and current, so as to enable the unit to be programmed for specific applications. Preferably, the power supply 212 includes selectively operable control means, including means for selectively controlling the amplitude of the output voltage and the amplitude of the beam generator current. A high-frequency, switch-mode power converter can be used to meet these requirements. The most appropriate topology for generating low power and high voltage is a resonant voltage converter working in conjunction with a high voltage, Cockroft-Walton-type multiplier. Low-power dissipation, switch-mode power-supply controller-integrated circuits (IC) are currently available for controlling such topologies with few ancillary components. A more detailed description of the power supply 212 is provided in U.S. Pat. Nos. 5,153,900 and 5,428,658.

The target assembly 210 preferably includes a target element 228 spaced apart from and opposite the electron emissive surface of the thermionic cathode 222, where the target element 228 has at least one radiation emissive element adapted to emit therapeutic radiation in response to incident accelerated electrons from the electron emissive surface of the thermionic cathode 222. In a preferred embodiment, the emitted therapeutic radiation consist of x-rays, however it should be noted that the scope of this invention is not limited to x-rays, and other forms of therapeutic radiation may also be generated.

In the present invention, the x-ray emissive target has a non-planar configuration. In a preferred embodiment, the target has a substantially conical configuration. Other embodiments of the invention may include targets having a substantially convex configuration, or a substantially hemispherical configuration, or a substantially spherical configuration. The target includes a thin, x-ray emissive film, and an x-ray transmissive support structure. By using a target having a non-flat configuration, and including an x-ray emissive film supported on an x-ray transmissive support structure, the radiation pattern around the target is rendered more uniform and intense.

The radiation generator assembly 201, which can be for example 1 to 2 cm-in length, extends from the end of the probe assembly 206 and includes a capsule 230 which encloses the target assembly. According to one embodiment, the radiation generator assembly 201 is rigid in nature and generally cylindrical in shape. In this embodiment the cylindrical capsule 230 enclosing the radiation generator assembly 201 can be considered to provide a substantially rigid housing 230 for the electron source 208. In one embodiment, the electron source 208 and the target assembly 210 is disposed within the capsule 230, with the thermionic cathode disposed at an input end of the capsule 230, and the target assembly 210 disposed at an output end of the housing 230. The capsule 230 defines a substantially evacuated interior region extending along the beam axis 209, between the thermionic cathode 222 at the input end of the capsule 230 and the target assembly 210 at the output end of the housing 230. The inner surface of the radiation generator assembly 201 is lined with an electrical insulator, while the external surface of the assembly is electrically conductive. According to a preferred embodiment, the radiation generator assembly 201 is hermetically sealed to the end of the probe assembly, and evacuated. According to another embodiment, the entire probe assembly 206 is evacuated.

The probe assembly 206 couples the laser source 204 and the high voltage power supply 212 to the target assembly 210. In the illustrated embodiment, the probe assembly 206 includes a flexible, electrically conductive catheter 205 extending along a probe axis between a proximal end and a distal end of the catheter 205. The probe assembly 206 includes optical delivery structure 213 having a proximal end 213A and a distal end 213B. The distal end 213B of the optical delivery structure 213 is affixed to the radiation generator assembly 201.

In a preferred embodiment, the optical delivery structure 213 is a flexible fiber optical cable. In this embodiment, the flexible catheter 205 that encloses the fiber optical cable 202 is a small-diameter, flexible, metallic outer tube. In this embodiment, the target assembly 210 includes an electrically conductive outer surface. Preferably, both the metallic tube 205 and the target element 228 are set at ground potential, in order to reduce the shock hazard of the device. In one embodiment, the fiber optical cable has a diameter of about 200 microns, and the flexible metallic tube 205 has a diameter of about 1.4 mm.

In a preferred embodiment, the fiber optic cable 213 includes an electrically conductive outer surface. For example, the outer surface of the fiber optic cable 213 may be made conductive by applying an electrically conductive coating. The electrically conductive outer surface of the fiber optic cable 213 provides a connection to the thermionic cathode 222 from the high voltage power supply 212. In this embodiment, the radiation generator assembly 201 also has an electrically conductive outer surface. Preferably, both the flexible metallic sheath 205 and the outer conductive surface of the radiation generator assembly 201 are set at ground potential in order to reduce the shock hazard of the device. The flexible sheath 205 couples a ground return from the target element 228 to the high voltage power supply 212, thereby establishing a high voltage field between the thermionic cathode 222 and the target element 228. In an exemplary embodiment, the fiber optic cable 213 may have a diameter of about 200 microns, and the flexible metallic sheath 205 may have a diameter of about 1.4 mm. A layer of dielectric material provides insulation between the outer surface of the fiber optic cable 213 and the inner surface of the metallic sheath 205.

Getters may be positioned within the housing 230. The getters aid in creating and maintaining a vacuum condition of high quality. The getter has an activation temperature, after which it will react with stray gas molecules in the vacuum. It is desirable that the getter used have an activation temperature that is not so high that the x-ray device will be damaged when heated to the activation temperature.

The thermionic cathode 222 has an electron emissive surface, and is typically formed of a metallic material. Suitable metallic materials forming the cathode 222 may include tungsten, thoriated tungsten, other tungsten alloys, and tantalum. In one embodiment, the cathode 222 may be formed by depositing a layer of electron emissive material on a base material, so that an electron emissive surface is formed thereon. By way of example, the base material may be formed from one or more metallic materials, including but not limited to Group VI metals such as tungsten, and Group II metals such as barium. In one form, the layer of electron emissive material may be formed from materials including, but not limited to, aluminum tungstate and scandium tungstate. The thermionic cathode 222 may also be an oxide coated cathode, where a coating of the mixed oxides of barium and strontium, by way of example, may be applied to a metallic base, such as nickel or a nickel alloy. The metallic base may be made of other materials, including Group VI metals such as tungsten. The thermionic cathode 222 has a non-planar configuration, designed to maximize the percentage of incident laser radiation that actually becomes absorbed by the thermionic cathode surface.

The fiber optical cable 202 is adapted to transmit laser radiation, generated by the laser source 204 (shown in FIG. 2(a)) and incident on the proximal end of the fiber optical cable assembly, to the distal end of the fiber optical cable assembly 213. The fiber optical cable 202 is also adapted to deliver a beam of the transmitted laser radiation to impinge upon the electron-emissive surface of the thermionic cathode 222. The beam of laser radiation must have a power level sufficient to heat at least a portion of the electron-emissive surface to an electron emitting temperature so as to cause thermionic emission of electrons from the surface.

In operation, the laser beam shining down the fiber optic cable 213 impinges upon the surface of the thermionic cathode 222, and rapidly heats the surface to an electron emitting temperature, below the melting point of the metallic cathode 222. Upon reaching of the surface of a electron emitting temperature, electrons are thermionically emitted from the surface. The high voltage field between the cathode 222 and the target element 228 (shown in FIGS. 2A and 2B accelerates these electrons, thereby forcing them to strike the surface of the target element 228 and produce x-rays. In one embodiment of the invention, a Nd:YAG laser was coupled into a SiO2 optical fiber having a diameter of 400 microns. A 20 kV power supply was used, and a thermionic cathode made of tungsten was used. With a thermionic cathode made of tungsten, just a few watts of power was needed to generate over 100 $\mu$A of electron current. In one example, an infrared diode laser was used to achieve about 100 $\mu$A of electron current, with only 180 mW of power.

Figure 3:
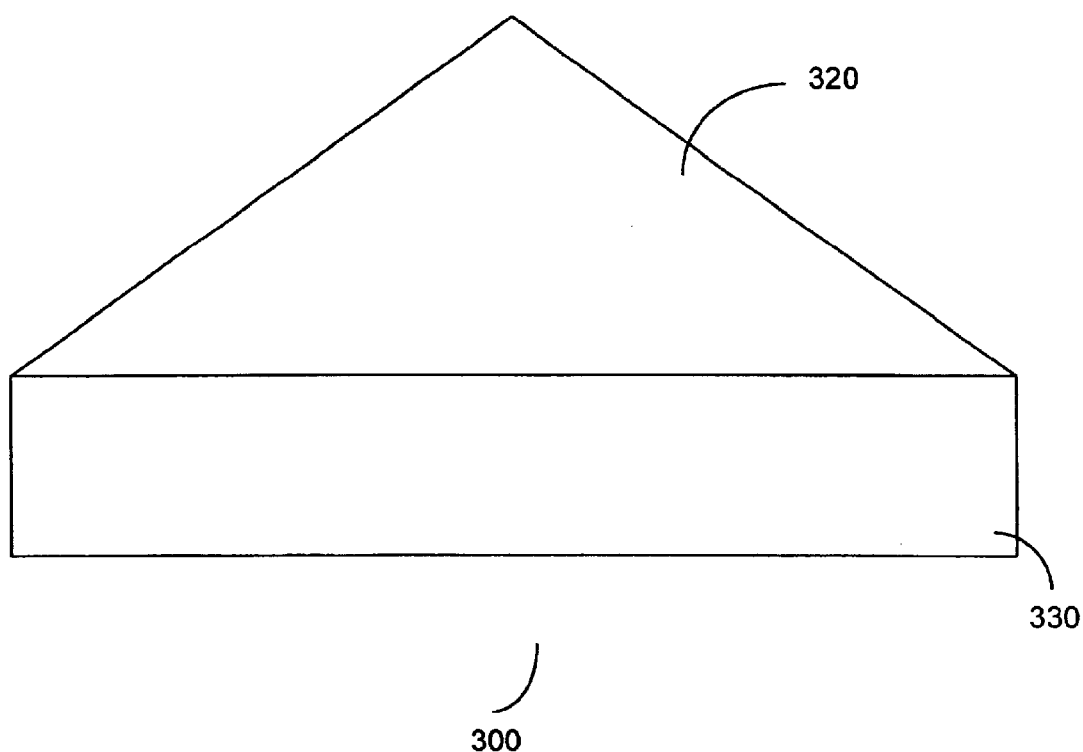
FIG. 3 illustrates an x-ray target constructed in accordance with the present invention and having a non-planar configuration adapted to increase the uniformity and intensity of the radiation pattern around the target.

FIG. 3 illustrates an x-ray target 300 constructed in accordance with the present invention, and having a non-planar configuration adapted to increase the uniformity and intensity of the radiation pattern around the target 300. In the present invention, the target geometry and configuration is selected so as to substantially reduce x-ray absorption that takes place within the target itself. The x-ray target 300 has a non-planar, curved surface, rather than a flat surface. The non-planar configuration of the x-ray target 300 serves to reduce the absorption of x-rays in the target 300, and also to spread out any remaining angular dependence of x-rays emitted from the target 300.

In the prior art, x-ray emissive targets have been used that consist of a planar, disk-shaped substrate made of an x-ray transmissive material, such as beryllium, and coated on the side exposed to the incident electron beam with a thin film or layer of a high-Z, x-ray emissive element, such as tungsten, uranium or gold. This type of target is disclosed, for example, in U.S. Pat. No. 5,153,900, entitled "Miniaturized Low Power X-Ray Source," and issued on Oct. 6, 1992 to Peter M. Nomikos et al. When the incident electron beam impinges upon a focal spot on the target, x-rays are emitted in all directions. As the emitted x-rays attempt to traverse the x-ray emissive thin film, some of the emitted x-rays become absorbed by the high-Z, x-ray emissive material in the thin film. With a completely flat target, the x-ray beam is completely attenuated in certain directions for which the x-rays must pass through a large amount of material. In those directions, a notch or cusp appears in the output radiation pattern. A cusp perpendicular to the probe axis, in what otherwise would be a spherical radiation field, is due to absorption within the target material itself. The x-ray path length in the target material, as well as absorption within the target material, is maximum in this perpendicular direction. In certain other directions, some level of transmission occurs for the emitted x-rays, and in other directions substantial transmission occurs. Flat, disk-shaped targets therefore cannot generate an isotropic x-ray radiation pattern.

A non-planar target, as implemented in the present invention, can generate a more isotropic emission of x-rays, as compared to a flat, planar target. Non-planar target geometries that are effective for purposes of the present invention include, but are not limited to, curved, hemispheric, conical, spherical, and convex target shapes. A curvature in the target serves both to reduce the absorption of x-rays in the target, and also to spread out any remaining angular dependence of x-rays emitted from the target.

One advantage of a conical, or other non-planar target is that an effect equivalent to x-ray beam steering can be achieved, by flooding the conical or otherwise non-planar surface of the target with electrons. X-ray beam steering is one method used in the prior art to homogenize the radiation pattern generated by the target, and is disclosed for example in the '900 patent. The electron beam generated from the cathode is "steered" or directed to selected surfaces on the target, for example where the target has different emission characteristics in different spatial regions. By directing the incident electron beam so that the electrons in the beam can land on all regions of the non-planar target surface, potential knots or notches in the output x-ray radiation pattern are compensated for, and the resulting effect is functionally equivalent to moving an electron beam that impinges upon a hemispheric or conical surface of a non-planar target.

In a preferred embodiment of the invention, illustrated in FIG. 3, the target 300 includes a thin film 320 supported on a support structure 330. The thin film 320 is made of a material that is substantially x-ray emissive. By way of example, the x-ray emissive material may include, but is not limited to, gold, tungsten, uranium, and molybdenum. The support structure 330 is made of a material that is substantially x-ray transmissive. The x-ray transmissive material may include, but is not limited to, beryllium and boron carbide.

In the illustrated preferred embodiment, the target 300 has the form of a conical frustum. In particular, the x-ray emissive thin film 320 has a substantially conical shape. The thin film may have a thickness of about one micron, although other sizes are also within the scope of the present invention. The x-ray emissive film 320 is placed upon an x-ray transmissive support structure that may be about 1 mm in length, although other sizes are also within the scope of this invention. By providing a non-planar target configuration, as disclosed in the present invention, the uniformity and intensity of the x-ray radiation pattern is substantially increased. The x-ray radiation generated by the target is thereby rendered more benign therapeutically.

While the invention has been particularly shown and described with reference to specific preferred embodiments, it should be understood by those skilled in the art that various changes in form and detail may be made therein without departing from the spirit and scope of the invention as defined by the appended claims.

What is claimed is:

1. A therapeutic radiation source, comprising:
   A. a radiation generator assembly, comprising:
      a. an electron source for emitting electrons to generate an electron beam along a beam path, said electron source including a thermionic cathode having an electron emissive surface, and
      b. a target positioned in said beam path, said target including means for emitting therapeutic radiation in response to incident accelerated electrons from said electron beam;
         wherein said target is characterized by a non-planar configuration;
   B. a source of optical radiation; and
   C. an optical delivery structure having a proximal end and a distal end and adapted for transmitting to said distal end optical radiation generated by said source and incident on said proximal end;
      wherein said optical delivery structure is adapted for directing a beam of said transmitted optical radiation upon a surface of said cathode, said beam of optical radiation having a power level sufficient to heat at least a portion of said surface to an electron emitting temperature so as to cause thermionic emission of electrons from said surface.

2. A therapeutic radiation source according to claim 1, wherein said target comprises:
   (a) a film made of a substantially x-ray emissive material; and
   (b) a support structure made of a substantially x-ray transmissive material.

3. A therapeutic radiation source according to claim 1, wherein said target includes an intersection edge and at least a first and a second substantially flat surface, each surface including a distal end, each surface extending outward from said intersection edge toward said distal end; and
   wherein said first surface and second surface form an angle with respect to each other.

4. A therapeutic radiation source according to claim 1, wherein said target has a substantially conical shape.

5. A therapeutic radiation source according to claim 1, wherein said target has a substantially convex shape.

6. A therapeutic radiation source according to claim 1, wherein said target has a substantially hemispherical shape.

7. A therapeutic radiation source according to claim 1, wherein said target has a substantially spherical shape.

8. A therapeutic radiation source according to claim 1, wherein said film has a thickness of about 1 micron.

9. A therapeutic radiation source according to claim 1, wherein said film is made of a material selected from the group consisting of gold, tungsten, uranium, and molybdenum.

10. A therapeutic radiation source according to claim 1, wherein said support structure has a length of about 1 mm.

11. A therapeutic radiation source according to claim 1, wherein said support structure is made of an x-ray transmissive material.

12. A therapeutic radiation source according to claim 1, further comprising:
   a substantially rigid housing enclosing said thermionic cathode and said target, wherein said housing defines a substantially evacuated interior region extending along said beam path between an input end and an output end of said housing.

13. A therapeutic radiation source according to claim 1, further comprising a radiation transmissive window at an output end of said housing, wherein therapeutic radiation emitted from said target is directed through said radiation transmissive window.

14. A therapeutic radiation source according to claim 1, wherein said optical delivery structure comprises a fiber optical cable.

15. A therapeutic radiation source according to claim 1, wherein said fiber optical cable has a diameter between about 100 microns to about 200 microns.

16. A therapeutic radiation source according to claim 1, wherein the power required for heating said electron emissive surface of said cathode so as to generate an electron beam forming a current of about 2 micro amps is between about 0.1 Watt to about 1.0 Watt.

17. A therapeutic radiation source according to claim 1, wherein said optical source is a laser, and wherein said beam of optical radiation is substantially monochromatic and coherent.

18. A therapeutic radiation source according to claim 1, wherein said therapeutic radiation comprises x-rays.

19. A therapeutic radiation source according to claim 1, further including means for providing an accelerating voltage between said electron source and said target element so as to establish an accelerating electric field which acts to accelerate electrons emitted from said electron source toward said target element.

20. A therapeutic radiation source according to claim 19, wherein said means for establishing an accelerating electric field is a power supply.

21. A therapeutic radiation source, comprising:
   A. a radiation generator assembly, comprising:
      a. an electron source for emitting electrons to generate an electron beam along a beam path, said electron source including a thermionic cathode having an electron emissive surface, and
      b. a target positioned in said beam path, said target including means for emitting therapeutic radiation in response to incident accelerated electrons from said electron beam; and c. a substantially rigid housing enclosing said thermionic cathode and said target, wherein said housing defines a substantially evacuated interior region extending along said beam path between an input end and an output end of said housing;

B. a source of optical radiation; and

C. an optical delivery structure having a proximal end and a distal end and adapted for transmitting to said distal end optical radiation generated by said source and incident on said proximal end, said optical delivery structure being adapted for directing a beam of said transmitted optical radiation upon a surface of said thermionic cathode, wherein said beam of optical radiation has a power level sufficient to heat at least a portion of said surface to an electron emitting temperature so as to cause thermionic emission of electrons from said surface; and wherein said target has a non-planar configuration.

22. A therapeutic radiation source according to claim 1, wherein said x-ray transmissive material is selected from the group consisting of beryllium and boron carbide.

* * * * *